United States Patent [19]

Puckette

[11] Patent Number: 4,912,276

[45] Date of Patent: Mar. 27, 1990

[54] PREPARATION OF BIARYL COMPOUNDS

[75] Inventor: Thomas A. Puckette, Longview, Tex.

[73] Assignee: Eastman Kodak Company, Rochester, N.Y.

[21] Appl. No.: 262,856

[22] Filed: Oct. 25, 1988

[51] Int. Cl.$^4$ ............................ C07C 2/02; C07C 1/20
[52] U.S. Cl. .................................. 585/425; 585/469; 562/466
[58] Field of Search ............................. 585/425, 469

[56] References Cited

U.S. PATENT DOCUMENTS

| | | | |
|---|---|---|---|
| 3,539,622 | 11/1970 | Heck | 260/515 |
| 3,636,168 | 1/1972 | Josephson | 260/645 |
| 3,748,350 | 7/1973 | Josephson | 260/475 |
| 4,105,705 | 8/1978 | Lareck | 260/668 |
| 4,263,466 | 4/1981 | Colon et al. | 585/421 |
| 4,694,109 | 9/1987 | Devon et al. | 568/454 |

OTHER PUBLICATIONS

Gilman and Lichtenwalter, Journal of the American Chemical Society, vol. 61, pp. 957–959 (1939), "Relative Reactivities of Organometallic Compounds, XXV, Coupling Reaction with Halides of Group VIII Metals".
Kharasch and Fields in the Journal of the American Chemical Society, vol. 63, pp. 2316–2320 (1941), "Factors Determining the Course and Mechanisms of Grignard Reactions, IV, The Effect of Metallic Halides on the Reaction of Aryl Grignard Reagents and Organic halides".
Corriu and Masse, J.C.S. Chemical Communications, 1972, p. 144, "Activation of Grignard Reagents by Transition-Metal Complexes, a New and Simple Synthesis of Trans-Stilbenes and Polyphenyls".
Kende et al., Tetrahderon Letters, 1975, pp. 3375–3378, "In Situ Generation of a Solvated, Zero-Valent Nickel Reagent, Biaryl Formation".
Tamao et al., Bulletin of the Chemical Society of Japan, vol. 49, pp. 1958–1969 (1976), "Nickel-Phosphine Complex-Catalyzed Grignard Coupling, I, Cross-Coupling of Alkyl, Aryl and Dalkenyl Grignard Reagents with Aryl and Alkenyl Halides: General Scope and Limitations".
Yamamoto et al., Bulletin of the Chemical Society of Japan, vol. 51, pp. 2091–2097 (1978), "A Novel Type of Polycondensation Utilizing Transition Metal-Catalyzed C-C. Coupling, I, Preparation of Thermostable Polyphenylene Type Polymers".
Chao et al., Journal of Organic Chemistry, vol. 48, pp. 1904–1907 (1983), "New Method for the Preparation of Activated Nickel and Cobalt Powders and Their Application in Biaryl Synthesis".
Colon & Kelsey, Journal of Organic Chemistry, vol. 51, pp. 2627–2637 (1986), "Coupling of Aryl Chlorides by Nickel and Reducing Metals".

*Primary Examiner*—Curtis R. Davis
*Attorney, Agent, or Firm*—S. E. Reiter; William P. Heath, Jr.

[57] ABSTRACT

A method for the preparation of biaryl compounds is disclosed which comprises contacting an aryl halide under conditions suitable to form a Grignard reagent and thereafter contacting the Grignard reagent with an aryl chloride in the presence of a catalyst comprising a nickel compound and a coordinating ligand under conditions suitable for the formation of biaryl compound. In an alternate embodiment of the present invention, biaryl compounds are prepared directly from aryl halides in a single reaction vessel by contacting aryl halide with elemental magnesium and a nickel catalyst comprising a nickel compound and a coordinating ligand in an aprotic, non-polar, ether-containing solvent system for a time and under conditions suitable for the formation of biaryl compound.

22 Claims, No Drawings

PREPARATION OF BIARYL COMPOUNDS

The present invention relates to the preparation of biaryl compounds from aryl halides. In a particular aspect, the present invention relates to the reductive coupling of aryl halides.

BACKGROUND OF THE INVENTION

It is known that biphenyl compounds can be produced by the reductive coupling of aryl halides. For example, Colon, et al., in U.S. Pat. No. 4,263,466, disclose the use of a metallic reducing agent such as zinc, magnesium, or manganese in a dipolar, aprotic solvent such as dimethylformamide with a catalyst containing a nickel compound in combination with organophosphines and alkali metal halide promoters. The reducing metal converts the nickel salts into highly reactive zerovalent nickel compounds which promote the coupling of the aryl halides and regenerate the nickel salts which can be reduced again to the zerovalent state, thereby maintaining the catalytic cycle.

Chao, et al., Journal of Organic Chemistry, Volume 48, pages 4904–4907 (1983), disclose a similar approach wherein aryl halides are reacted with an equivalent amount of a highly activated metal such as nickel powder.

An alternative approach is to activate an aryl halide by a chemical transformation, and then allow the activated aryl halides to couple to form biaryls species. For example, Gilman, et al., in the Journal of the American Chemical Society, Volume 61, pages 957–959 (1939), demonstrated this approach by the reaction of two equivalents of aryl Grignard reagents with one equivalent of nickel (II) salts to give biaryl compounds. This reaction is believed to proceed through the bis aryl nickel species which then decomposes to give the desired biaryl product.

More recently, Kumada, et al., in Bulletin of the Chemical Society of Japan, Volume 49, pages 1958–1969 (1976), have demonstrated that aryl halides can be reacted with a variety of aliphatic Grignard reagents to give alka-aryl products. However, attempts to couple aryl Grignard reagents with aryl halides were successful only with aryl bromides. Attempts to use aryl chlorides predictably gave less than a ten percent yield of desired biaryl products. These results are not surprising since it is well known in the art that aryl chlorides are generally less reactive than their bromide or iodide analogs.

Aryl chlorides are frequently more readily available than are the corresponding bromides and iodides. The chlorides are also typically less expensive materials as well. It would, therefore, be desirable to find a means to promote the coupling of aryl chlorides to produce high yields of biaryl compounds.

STATEMENT OF THE INVENTION

In accordance with the present invention, it has been found that aryl chlorides can be reductively coupled to produce biaryl compounds in high yield. By contacting approximately equimolar quantities of an aryl chloride with an aryl Grignard reagent under reductive coupling conditions, high yields of biaryl compounds are obtained.

The invention method also makes possible the preparation of unsymmetrical biaryl compounds as one aryl moiety can be employed for preparation of the Grignard reagent while a second aryl moiety can be employed as the aryl chloride. Thus, a convenient method is provided for preparing unsymmetrical biaryl compounds.

Alternatively, approximately two equivalents of an aryl halide can be contacted with about one equivalent of elemental magnesium. This contacting is carried out under conditions such that intermediate Grignard reagent, as formed, reacts with additional aryl halide to form biaryl compounds. Thus, this alternate embodiment of the present invention leads to the production of biaryl compounds from aryl halide compounds in a single vessel. This embodiment has the advantage of reduced requirements for materials handling. Thus, exposure to air of such air sensitive materials such as Grignard reagents is minimized. In addition, handling losses, product contamination and the like are also greatly reduced.

The practice of the present invention allows for the ready preparation of biaryl derivatives from aryl halide starting materials, including aryl chlorides. Aryl chlorides are generally preferred starting materials as they are more accessible on a commercial basis and are generally less expensive than the corresponding aryl bromides or aryl iodides.

DETAILED DESCRIPTION OF THE INVENTION

In accordance with the present invention, there is provided a method for the preparation of biaryl compounds of the structure.

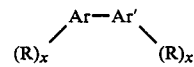

wherein each of Ar and Ar' are independently an aromatic moiety having in the range of 6 up to 14 carbon atoms, each R is independently selected from the group consisting of:

hydrocarbyl substituents having in the range of 1 up to 20 carbon atoms,

—OR', wherein R' is a hydrocarbyl radical having in the range of 1 up to 20 carbon atoms, and protected carbonyl-containing derivatives thereof, wherein x is an integer falling in the range of 0 up to 8, depending on the size of the aromatic ring (i.e., Ar and Ar').

The invention method comprises (a) contacting an aryl halide having the structure:

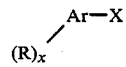

wherein Ar, R and x are as defined above and X is a halogen; with elemental magnesium under conditions suitable for the formation of a Grignard reagent having the structure Ar—MgX, and thereafter, (b) contacting said Grignard reagent with in the range of about 0.8 up to 2 molar equivalents, based on the moles of Grignard reagent, of an aryl chloride having the structure:

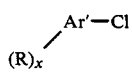

wherein Ar', R and x are as defined above, and at least 0.001 equivalents of a specific nickel catalyst.

The nickel catalyst contemplated for use in the practice of the present invention comprises:

(I) zerovalent nickel or a nickel compound precursor thereof, and (II) a coordinating ligand comprising a triorganophosphine, and optionally, at least one bidentate ligand containing at least one nitrogen atom as part of an aromatic ring structure, wherein said contacting is carried out in an aprotic, non-polar, solvent system for a time and under conditions suitable for the formation of the desired biaryl compound.

In accordance with a specific embodiment of the present invention, there is further provided a method for the preparation in a single reaction vessel of biaryl compounds of the structure:

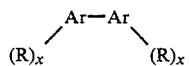

wherein Ar is an aromatic moiety having in the range of 6 up to 14 carbon atoms, R is selected from the group consisting of:

hydrocarbyl substituents having in the range of 1 up to 20 carbon atoms,

—OR', wherein R' is a hydrocarbyl radical having in the range of 1 up to 20 carbon atoms, and protected carbonyl-containing derivatives thereof; wherein x is an integer falling in the range of 0 up to 8, depending on the size of the aromatic ring (i.e., Ar).

The invention method comprises contacting, in a single reaction vessel, an aryl halide having the structure:

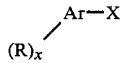

wherein Ar, R and x are as defined above and X is a halogen; with elemental magnesium and at least 0.001 equivalents of a specific nickel catalyst. In a preferred aspect of this embodiment of the present invention, the aryl chlorides are preferably employed.

The nickel catalyst contemplated for use in the practice of the present invention comprises:

(a) zerovalent nickel or a nickel compound precursor thereof, and (b) a coordinating ligand comprising an organophosphine, and optionally, at least one bidentate ligand containing at least one nitrogen atom as part of an aromatic ring structure, wherein said contacting is carried out in an aprotic, non-polar, ether-containing solvent system for a time and under conditions suitable for the formation of the desired biaryl compound.

Aryl halides contemplated for use in the practice of the present invention are compounds having the general structure:

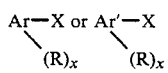

wherein each of Ar and Ar' are independently aromatic moieties having in the range of 6 up to 14 carbon atoms, each R is independently selected from the group consisting of:

hydrocarbyl substituents having in the range of 1 up to 20 carbon atoms,

—OR', wherein R' is a hydrocarbyl radical having in the range of 1 up to 20 carbon atoms, and protected carbonyl-containing derivatives thereof;

wherein x is an integer falling in the range of 0 up to 8, depending on the size of the aromatic ring (i.e., Ar and Ar').

Exemplary aryl halides contemplated for use in the practice of the present invention include:
2-chlorotoluene,
2-bromotoluene,
4-chlorotoluene,
4-bromotoluene,
2-chloro-4-methylnaphthalene,
2-bromo-4-methylnaphthalene,
4-chloroanisole,
4-bromoanisole,
2-chlorobenzyl(2-methoxy)ethyl ether,
2-bromobenzyl(2-methoxy)ethyl ether,
2-chlorobenzyl methyl ether,
2-bromobenzyl methyl ether,
2-chlorobenzyl ethyl ether,
2-bromobenzyl ethyl ether,
and the like, as well as mixtures of any two or more thereof.

When the invention process is carried out as a two-step procedure, the first step involves converting a portion of the aryl halide into a Grignard reagent. Means for converting aryl halides into aryl Grignard reagents are well within the capabilities of those of skill in the art.

When the invention process is carried out in one reaction vessel, the molar ratio of elemental magnesium to aryl halide can be varied widely, typically falling within the range of 0.25:1 up to 5:1.(moles of magnesium per mole of aryl halide). Preferably, this molar ratio falls within the range of about 0.3:1 up to 1:1, with molar ratios in the range of about 0.45:1 up to 0.6:1 being most preferred.

A wide range of nickel compounds are suitable for use in the practice of the present invention, so long as the nickel compounds employed are essentially water-free. The nickel (II) halide salts are a convenient source of nickel as such compounds are readily available in anhydrous form. Alternatively, hydrates of such compounds can be employed where appropriate means for removal of water, e.g., azeotropic distillation, is employed prior to contacting of the nickel species with Grignard reagent or elemental mgnesium/aryl halide combinations. Those of skill in the art recognize that a wide variety of other nickel compounds can be used, e.g., nickel nitrates, sulfates, phosphates, oxides, carbonates, carboxylates, acetylacetonate and the like, as well as Ni(O) complexes such as, for example, bis(1,5-cyclooctadienyl)nickel(O), nickel(O) tetracarbonyl, and the like.

The nickel (II) halides are presently preferred because of their ready availability in anhydrous form, or ease of preparation in substantially anhydrous form from the hydrated species.

Organophosphines contemplated for use in the practice of the present invention are compounds of the structure:

PR$_3$ or R$_2$P—Y—PR$_2$ wherein each R is independently selected from the group consisting of hydrocarbyl substituents having in the range of 1 up to 20 carbon atoms, halogens, alkoxy moieties, aryloxy moieties, and the like, as well as substituted derivatives thereof; and Y is selected from alkylene, alkenylene, arylene, biarylene, and the like bridging groups having in the range of 1 up to 30 carbon atoms.

Exemplary organophosphines include triphenylphosphine, tricyclohexylphosphine, tribenzylphosphine, 2,2'-bis(diphenylphosphinomethyl)-1,1'-biphenyl, 1,6-bis(diphenylphosphino)hexane, and the like, as well as mixtures of any two or more thereof.

Optional coordinating ligands employed in combination with the organophosphines are bidentate ligands containing at least one nitrogen atom as part of an aromatic ring structure. Such bidentate ligands include bipyridine, a $C_1$ up to $C_6$ dialkylamino pyridine, phenanthroline or 2-picolinic acid, and the like. Alternatively, such bidentate ligands can be produced in situ by charging a heteroaryl halide to the reaction mixture (e.g., as demonstrated in Example 3 below). Under the reaction conditions and in the presence of the nickel and magnesium species, the heteroaryl halide is readily converted into a bidentate ligand wherein both of the heteroatoms are part of aromatic ring structures.

When mixture of organophosphine and bidentate ligand containing at least one nitrogen atom as part of an aromatic ring structure are employed as the coordinating ligand, molar ratios of organophosphine to the bidentate ligand can vary widely, for example, in the range of about 1:1 up to 20:1.

The molar ratio of coordinating ligands to nickel compound employed in the practice of the present invention can vary widely. Typically, such molar ratios will fall within the range of 0.5:1 up to 20:1, with ratios in the range of about 2:1 up to 10:1 preferred.

The molar ratio of Grignard reagent to nickel compound employed in the practice of the present invention can vary widely. Typically, such ratio falls within the range of about 10:1 up to 1000:1, with molar ratios in the range of about 20:1 up to 400:1 preferred.

Solvents suitable for use in the practice of the present invention are typically ether-type solvents in which Grignard reagents can be readily prepared. Typical ether-type solvents suitable for use in the practice of the present invention include diethyl ether, dibutyl ether, tetrahydrofuran, 1,4-dioxane, glyme, diglyme, and the like, as well as mixtures of any two or more thereof. Optionally, substantial quantities of an aromatic hydrocarbon having in the range of about 6 up to 15 carbon atoms can be employed in a mixture with the ether-type solvent. The solvent system employed in the practice of the present invention should contain sufficient ether-type solvent to maintain the formed Grignard reagent substantially in solution. Up to about 80 volume percent of the solvent system can comprise such aromatic hydrocarbons. When used, preferred aromatic hydrocarbons include benzene, toluene, or xylene.

The reaction conditions under which aryl Grignard reagent and aryl chloride are contacted can vary widely. Typically such contacting is carried out at a temperature in the range of about 0° up to 150° C. Preferred reaction temperatures fall within the range of about 50° up to 110° C.

Similarly, reaction time employed for contacting of aryl Grignard reagent and aryl chloride can vary widely. Suitable reaction times fall within the range of about 2 up to 48 hours or longer. Preferred reaction times fall within the range of about 4 up to 16 hours.

When the invention process is carried out in one reaction vessel, the reaction temperature employed typically falls in the range of about 0° up to 150° C., with reaction times typically falling in the range of about 2 up to 48 hours. Preferred reaction condition comprise temperatures in the range of about 50° up to 110° C. for times in the range of about 4 up to 16 hours.

When the invention process is carried out in one vessel, i.e., all reagents (aryl halide, elemental magnesium, nickel compound and coordinating ligand(s)) are charged to the reaction vessel at one time, it is preferred that a combination of coordinating ligands be employed. Presently preferred combinations comprise at least one organophosphine and at least one bidentate ligand containing at least one nitrogen atom as part of an aromatic ring structure. Molar ratios of organophosphine to bidentate employed for this purpose can vary broadly from about 1:1 up to 20:1. Preferred molar ratios fall within the range of about 2 up to 10.

Reaction workup and product recovery can be carried out employing standard techniques well known by those of skill in the art.

The present invention will now be described in greater detail by reference to the following non-limiting examples.

EXAMPLE 1

Two Step Procedure for the Preparation of 2,2'-Dimethyl-1,1'-biphenyl

To a nitrogen purged, 0.5 liter three neck flask equipped with a reflux condenser, stirring bar, and thermometer was charged magnesium turnings (8.75 grams, 0.360 mole), 2-chlorotoluene (37.95 grams, 0.300 mole), tetrahydrofuran (THF; 150 mL) and toluene (150 mL). The mixture was stirred and then a solution of o-tolylmagnesium chloride (0.5 mL of 2.0 Molar solution in THF) was added. The resulting mixture was heated with stirring to 85° C. for 12 hours and then cooled to room temperature. The solution was decanted away from the remaining magnesium fines into an addition funnel.

To a nitrogen purged, 1.0 liter three neck flask equipped with a reflux condenser and mechanical stirrer was charged anhydrous nickel (II) bromide (0.33 grams, 1.5 mmole), triphenylphosphine (3.93 grams, 15 mmole), 2-chlorotoluene (34.16 grams, 0.270 mole), THF (100 mL), and toluene (100 mL). The reaction mixture was stirred and heated to 70° C., and the Grignard solution prepared as described in the preceding paragraph was added dropwise over a 35-minute period. The temperature of the reaction mixture gradually rose to the reflux temperature of the solvent (about 85° C.). The reflux was continued for an additional two hours after addition of the Grignard solution was completed. The reaction mixture was then cooled to ambient and quenched by the addition of 250 mL of 6 percent hydrochloric acid. The layers were separated, and the organic phase was washed with 200 mL of saturated sodium chloride solution. The layers were separated and 0.96 gram of t-butyltoluene was added to the product solution as an internal standard. Gas chromatography analysis showed that the solution contained 47.6 grams of 2,2'-dimethyl-1,1'-biphenyl (97 percent of theory).

EXAMPLE 2

Procedure for the Preparation of 2,2'-Dimethyl-1,1'-biphenyl in a Single Reaction Vessel Using Bipyridine To a nitrogen purged three neck 1.0 liter flask equipped with a reflux condenser and mechanical stirrer was charged anhydrous nickel bromide (0.27 grams, 1.25 mmole), bipyridine (0.39 grams, 2.5 mmole), triphenylphosphine (2.62 grams, 10 mmole), magnesium turnings (6.68 grams, 0.275 mole), 2-chlorotoluene (63.25 grams, 0.500 mole), toluene (200 mL) and THF (200 mL). Preformed o-tolylmagnesium chloride (1.0 mL of 2.0 molar solution) was added and the reaction mixture was stirred and heated to reflux for 12 hours. The reaction mixture was then cooled to ambient and quenched by the addition of 250 mL of 6 percent hydrochloric acid. The mixture was stirred until all the magnesium fines had been consumed and then the layers were separated. The organic phase was washed with 200 mL of saturated sodium chloride and the layers separated. Tertiary butyltoluene (1.00 grams) was added to the reaction mixture as an internal standard and gas chromatographic analysis of the mixture showed the presence of 39.4 grams of 2,2'-dimethyl-1,1'-biphenyl in the reaction mixture (86.6 percent of theory).

EXAMPLE 3

Single Vessel Procedure for the Preparation of 2,2'-Dimethyl-1,1'-biphenyl Using 2-Bromopyridine To a nitrogen purged three neck 1.0 liter flask equipped with a reflux condenser and mechanical stirrer was charged anhydrous nickel bromide (0.27 grams, 1.25 mmole), 2-bromopyridine (0.80 grams, 5.0 mmole), triphenylphosphine (2.62 grams, 10 mmole), magnesium turnings (7.29 grams, 0.300 mole), 2-chlorotoluene (63.25 grams, 0.500 mole), toluene (200 mL) and THF (200 mL). Preformed o-tolylmagnesium chloride (1.5 mL of 2.0 molar solution) was added and the reaction mixture was stirred and heated to reflux for 12 hours. The reaction mixture was then cooled to ambient and quenched by the addition of 250 mL of 6 percent hydrochloric acid. The mixture was stirred until all the magnesium fines had been consumed and then the layers were separated. The organic phase was washed with 250 mL of saturated sodium chloride and the layers separated. Tertiary butyltoluene (1.00 grams) was added to the reaction mixture as an internal standard and gas chromatographic analysis of the mixture showed the presence of 38.8 grams of 2,2'-dimethyl-1,1'-biphenyl in the reaction mixture (85.3 percent of theory).

The invention has been described in detail with particular reference to preferred embodiments thereof, but it will be understood that variations and modifications can be effected within the spirit and scope of the invention.

I claim:

1. A method for the preparation of biaryl compounds of the structure:

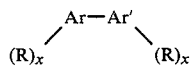

wherein each of Ar and Ar' are independently an aromatic moiety having in the range of 6 up to 14 carbon atoms, each R is independently selected from the group consisting of:
 hydrocarbyl substituents having in the range of 1 up to 20 carbon atoms,
 —OR', wherein R' is a hydrocarbyl radical having in the range of 1 up to 20 carbon atoms, and
 protected carbonyl-containing derivatives thereof; and
wherein x is an integer falling in the range of 0 up to 8, depending on the size of the aromatic ring, Ar and Ar';

said method comprising
 (a) contacting an aryl halide having the structure:

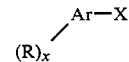

wherein Ar, R and x are as defined above and X is a halogen; under conditions suitable for the formation of a Grignard reagent having the structure

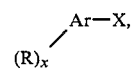

and thereafter,
 (b) contacting said Grignard reagent with in the range of about 0.8 up to 2 molar equivalents, based on the moles of Grignard reagent, of an aryl chloride having the structure:

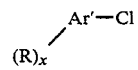

wherein Ar', R and x are as defined above, and at least 0.001 equivalents of a nickel catalyst comprising:
 (I) zerovalent nickel or a nickel compound precursor thereof, and
 (III) a coordinating ligand comprising an organophosphine, wherein said organophosphine is selected from triphenylphosphine, tricyclohexylphosphine, tribenzylphosphine, 2,2'-bis(diphenylphosphinomethyl)-1,1'-biphenyl, or 1,6-bis(diphenylphosphino)hexane, and optionally, at least one bidentate ligand containing at least one nitrogen atom as part of an aromatic ring structure,
 wherein said contacting is carried out in an aprotic, non-polar, ether-containing solvent system for a time and under conditions suitable for the formation of the desired biaryl compound.

2. The method of claim 1 wherein said aryl chloride is selected from the group consisting of:
 2-chlorotoluene,
 4-chlorotoluene,
 2-chloro-4-methylnaphthalene,
 4-chloroanisole,
 2-chlorobenzyl(2-methoxy)ethyl ether,
 2-chlorobenzyl methyl ether,
 2-chlorobenzyl ethyl ether,
 as well as mixtures of any two or more thereof.

3. The method of claim 1 wherein the molar ratio of coordinating ligand to nickel compound falls within the range of about 0.5 up to 20:1.

4. The method of claim 3 wherein the molar ratio of Grignard reagent to nickel compound falls within the range of about 10 up to 1000:1.

5. The method of claim 1 wherein said coordinating ligand comprises a mixture of organophosphine and a bidentate ligand containing at least one nitrogen atom as part of an aromatic ring structure in a molar ratio in the range of about 1 up to 20:1.

6. The method of claim 5 wherein said bidentate ligand is selected from bipyridine, a $C_1$ up to $C_6$ dialkylamino pyridine, phenanthroline or 2-picolinic acid.

7. The method of claim 1 wherein said ether-containing solvent system is selected from the group consisting of:
   diethyl ether,
   dibutyl ether,
   tetrahydrofuran,
   1,4-dioxane,
   glyme,
   diglyme,
as well as mixtures of any two or more thereof, in the further presence of 0 up to 80 volume percent of an aromatic hydrocarbon having in the range of about 6 up to 15 carbon atoms.

8. The method of claim 7 wherein said aromatic hydrocarbon is selected from benzene, toluene or xylene.

9. The method of claim 1 wherein said contacting of Grignard and aryl chloride is carried out at a temperature in the range of about 0° up to 150° C. and for time in the range of about 2 up to 48 hours.

10. A method for the preparation of biaryl compounds of the structure:

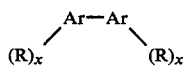

wherein Ar is an aromatic moiety having in the range of 6 up to 14 carbon atoms, R is selected from the group consisting of:
   hydrocarbyl substituents having in the range of 1 up to 20 carbon atoms,
   —OR', wherein R' is a hydrocarbyl radical having in the range of 1 up to 20 carbon atoms, and
   protected carbonyl-containing derivatives thereof; and
wherein x is an integer falling in the range of 0 up to 8, depending on the size of the aromatic ring, Ar;
said method comprising contacting an aryl halide having the structure:

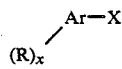

wherein Ar, R and x are as defined above and X is a halogen; with elemental magnesium and at least 0.001 equivalents of a nickel catalyst comprising;
(a) zerovalent nickel or a nickel compound precursor thereof, and
(b) a coordinating ligand comprising an organophosphine, and optionally, at least one bidentate ligand containing at least one nitrogen atom as part of an aromatic ring structure,
wherein said contacting is carried out in an aprotic, non-polar, ether-containing solvent system for a time and under conditions suitable for the formation of the desired biaryl compound.

11. The method of claim 10 wherein said aryl halide is selected from the group consisting of:
   2-chlorotoluene,
   2-bromotoluene,
   4-chlorotoluene,
   4-bromotoluene,
   2-chloro-4-methylnaphthalene,
   2-bromo-4-methylnaphthalene,
   4-chloroanisole,
   4-bromoanisole,
   2-chlorobenzyl(2-methoxy)ethyl ether,
   2-bromobenzyl(2-methoxy)ethyl ether,
   2-chlorobenzyl methyl ether,
   2-bromobenzyl methyl ether,
   2-chlorobenzyl ethyl ether,
   2-bromobenzyl ethyl ether,
as well as mixtures of any two or more thereof.

12. The method of claim 10 wherein said aryl halide is selected from the group consisting of:
   2-chlorotoluene,
   4-chlorotoluene,
   2-chloro-4-methylnaphthalene,
   4-chloroanisole,
   2-chlorobenzyl(2-methoxy)ethyl ether,
   2-chlorobenzyl methyl ether,
   2-chlorobenzyl ethyl ether,
as well as mixtures of any two or more thereof.

13. The method of claim 10 wherein the molar ratio of coordinating ligand to nickel compound falls within the range of about 0.5 up to 20:1.

14. The method of claim 13 wherein the molar ratio of aryl halide to nickel compound falls within the range of about 10 up to 1000:1.

15. The method of claim 14 wherein the molar ratio of elemental magnesium to aryl halide falls within the range of about 0.25 up to 5:1.

16. The method of claim 14 wherein the molar ratio of elemental magnesium to aryl halide falls within the range of about 0.3:1 up to 1:1.

17. The method of claim 10 wherein said coordinating ligand comprises a mixture of organophosphine and a bidentate ligand containing at least one nitrogen atom as part of an aromatic ring structure in a molar ratio in the range of about 1 up to 20:1.

18. The method of claim 17 wherein said organophosphine is selected from triphenylphosphine, tricyclohexylphosphine, tribenzylphosphine, 2,2'-bis(diphenylphosphinomethyl)-1,1'-biphenyl or 1,6-bis(diphenylphosphino)hexane.

19. The method of claim 17 wherein said bidentate ligand is selected from bipyridine, a $C_1$ up to $C_6$ dialkylamino pyridine, phenanthroline or 2-picolinic acid.

20. The method of claim 10 wherein said ether-containing solvent system is selected from the group consisting of:
   diethyl ether,
   dibutyl ether,
   tetrahydrofuran,
   1,4-dioxane,
   glyme,
   diglyme,
as well as mixtures of any two or more thereof, in the further presence of 0 up to 80 volume percent of an aromatic hydrocarbon having in the range of about 6 up to 15 carbon atoms.

21. The method of claim 20 wherein said aromatic hydrocarbon is selected from benzene, toluene, or xylene.

22. The method of claim 10 wherein said contacting is carried out at a temperature in the range of about 0° up to 150° C. and for time in the range of about 2 up to 48 hours.

* * * * *